United States Patent [19]
El-Hage et al.

[11] Patent Number: 5,843,378
[45] Date of Patent: Dec. 1, 1998

[54] METHOD OF PRODUCING A PROBE FOR ASPIRATING AND DISPENSING PROBE HAVING SURFACE SENSING CAPABILITY

[75] Inventors: Amer El-Hage, Menlo Park; Rick V. Stellmacher, Cupertino, both of Calif.

[73] Assignee: LJL Biosystems, Sunnyvale, Calif.

[21] Appl. No.: 790,096

[22] Filed: Jan. 29, 1997

Related U.S. Application Data

[63] Continuation-in-part of Ser. No. 524,019, Sep. 5, 1995, abandoned.

[51] Int. Cl.$^6$ ........................................................ B01L 3/02
[52] U.S. Cl. ............................... 422/180; 422/63; 422/67; 422/99; 73/863.32; 73/864.01; 73/864.14; 73/864.21; 436/180
[58] Field of Search ................................ 422/50, 63, 64, 422/65, 66, 67, 99, 100, 102, 103, 104; 73/863.32, 864.01, 864.14, 864.21; 436/180

[56] References Cited

U.S. PATENT DOCUMENTS

| | | | |
|---|---|---|---|
| 3,754,444 | 8/1973 | Ure et al. | 73/863.01 |
| 4,451,433 | 5/1984 | Yamashita et al. | 422/63 |
| 4,647,432 | 3/1987 | Wakatake | 422/64 |
| 5,004,582 | 4/1991 | Miyata et al. | 422/56 |
| 5,045,286 | 9/1991 | Kitajima et al. | 422/100 |
| 5,178,835 | 1/1993 | Uekusa et al. | 422/66 |

*Primary Examiner*—Harold Y. Pyon
*Attorney, Agent, or Firm*—Lumen Intellectual Property Services

[57] ABSTRACT

A method of producing a probe for aspirating and dispensing liquid. A fluid conduit and rod are positioned in the central bore of a tube so that an inlet end of the conduit and a contact end of the rod protrude from an upper end of the tube and a discharge end of the conduit and a sensing end of the rod protrude from a lower end of the tube. The tube has a heat-shrinkable outer layer and a meltable inner layer. The tube is heated so that its outer layer shrinks and its inner layer melts to encapsulate middle portions of the conduit and rod. A circuit board having first and second traces and first and second holes is placed on the upper end of the tube so that the inlet end of the conduit is inserted through the first hole and the contact end of the rod is inserted through the second hole. The conduit and rod are attached to the board so that the conduit is electrically connected to the first trace and the rod is electrically connected to the second trace. First and second conducting pins are also attached to the board. The conducting pins electrically connect the traces to a voltage sensing circuit when the probe is attached to a probe positioning device.

12 Claims, 4 Drawing Sheets

5,843,378

METHOD OF PRODUCING A PROBE FOR ASPIRATING AND DISPENSING PROBE HAVING SURFACE SENSING CAPABILITY

CONTINUATION APPLICATION INFORMATION

This application is a continuation in part of application Ser. No. 08/524,019 filed on Sep. 5, 1995, now abandoned.

FIELD OF THE INVENTION

The present invention relates generally to probes for chemical analysis, and in particular to a method for producing an aspirating and dispensing probe having surface sensing capability.

DESCRIPTION OF PRIOR ART

Aspirating and dispensing probes are often used to transfer liquids between various vessels and compartments in a chemical analyzer. The liquids typically include samples to be tested and reagents for testing the samples. The samples and reagents are usually placed in vessels which are mounted on a carousel. An aspirating and dispensing probe is attached to a probe positioning device, such as a mechanical arm, which positions the probe in an appropriate vessel. The probe aspirates an aliquot of sample liquid from the vessel and dispenses the sample liquid in a reaction cuvette. The probe then successively aspirates reagents from reagent vessels and transfers the reagents to the reaction cuvette. After the sample-reagent mixture incubates in the reaction cuvette, the probe transfers the reaction products to an analysis chamber.

To aspirate a correct quantity of liquid, the tip of the probe must be immersed in the liquid. If the tip is not immersed, the probe aspirates unwanted air bubbles. A sample aliquot has a volume on the order of a few microliters so that the aspiration of only a few air bubbles greatly reduces the relative quantity of aspirated liquid. A surface detection mechanism is typically used to detect if the probe is immersed. A conventional resistive detector measures the resistance between two electrically insulated electrodes. One of the electrodes is attached to the probe, and the other electrode is either attached to the probe or in contact with the liquid at all times.

When the probe is immersed in liquid, the liquid places a finite resistance between the two electrodes. This resistance between the electrodes signals that the probe is in contact with the liquid. One problem with conventionally designed probes is that a finite resistance may exist between the electrodes even when the probe is not immersed. A liquid droplet may form on the tip of the probe and establish contact with each electrode. The liquid droplet causes the detector to signal that the probe is immersed when the probe merely has a droplet connecting the electrodes.

A second problem with conventionally designed probes is that each probe must be frequently washed to remove contaminants.

A washing station is typically provided to wash the probe between aspirations of different substances. However, washing the probe does not guarantee the removal of all contaminants from the probe. The presence of contaminants carried over from previously probed samples causes potentially inaccurate test results. It is therefore desirable to replace the probe as often as possible. Unfortunately, the cost of manufacturing probes using conventional production techniques makes frequent probe replacement impractical.

One such probe produced by conventional techniques is disclosed in U.S. Pat. No. 4,451,433 issued to Yamashita et al. on May 29, 1984. Yamashita describes a probe having an electrode and an electrically conductive pipetting tube. The electrode and pipetting tube form a liquid level sensor for detecting if the probe tip is immersed. To assemble the probe, the electrode is first coated with an electrically insulative coating. The pipetting tube and electrode are further coated with an outer insulative tube. The pipetting tube is also paired with an electrode wire connecting the pipetting tube to a liquid level detection circuit.

The probe production method taught by Yamashita requires two separate coating steps, increasing the cost and complexity of the probe. Moreover, Yamashita does not teach any method of producing the probe with an attachment mechanism for easily attaching the probe to a mechanical arm. Further, Yamashita does not teach any method for producing the probe with a tip whose shape reduces the likelihood of a liquid droplet establishing contact between the pipetting tube and electrode. Thus, the probe disclosed by Yamashita is impractical for frequent probe replacement and potentially inaccurate in its sensing of probe tip immersion.

Another probe is disclosed in U.S. Pat. No. 5,045,286 issued to Kitajima et al. on Sep. 3, 1991. Kitajima describes a probe having two electrodes longitudinally embedded in a hollow injection nozzle. The probe is fabricated by injection molding insulation resin to form two separate nozzle halves, each half being produced independently of the other. The two halves are placed in a die and conductive resin is injection molded between the halves to form the two electrodes.

The probe production method taught by Kitajima requires at least three separate injection molding steps, increasing the cost and complexity of manufacturing the probe. Moreover, Kitajima does not teach any method for producing the probe with a tip whose shape reduces the likelihood of a liquid droplet establishing contact between the conductive resin electrodes. Thus, the probe disclosed by Kitajima is potentially inaccurate in its sensing of tip immersion.

OBJECTS AND ADVANTAGES OF THE INVENTION

In view of the above, it is a primary object of this invention to provide a method for producing a low cost, disposable probe for aspirating and dispensing liquids. It is another object of the invention to provide a method for producing a probe having a shape which reduces errors in surface sensing measurements. It is a further object of the invention to provide a method for producing a probe which may be easily attached to a probe positioning device and easily detached from the device.

These and other objects and advantages will become more apparent after consideration of the ensuing description and the accompanying drawings.

SUMMARY OF THE INVENTION

The invention presents a method of producing a probe for aspirating and dispensing liquid. The method includes the step of providing an electrically insulative tube, an electrically conductive fluid conduit, and an electrically conductive rod. The tube has upper and lower ends, a heat-shrinkable outer layer, a meltable inner layer, and a central bore extending the length of the tube. The inner layer has a lower melting point than the outer layer. The conduit has an inlet end, a discharge end, and a middle section between the inlet and discharge ends. The rod has a contact end, a sensing end, and a middle portion between the contact and sensing ends.

The method also includes the step of positioning the conduit and rod in the central bore such that the inlet end of the conduit and the contact end of the rod protrude from the upper end of the tube and such that the discharge end of the conduit and the sensing end of the rod protrude from the lower end of the tube. The tube is heated so that the outer layer shrinks and the inner layer melts to encapsulate the middle section of the conduit and the middle portion of the rod. The middle section of the conduit and the middle portion of the rod are encapsulated such that the conduit is electrically insulated from the rod.

In the preferred embodiment, the method includes an additional step of providing a board having a first hole for receiving the inlet end of the conduit and a second hole for receiving the contact end of the rod. The board also has first and second electrically conductive traces which are electrically insulated from each other. The inlet end of the conduit is inserted through the first hole and the contact end of the rod is inserted through the second hole. The conduit and rod are then attached to the board such that the conduit is electrically connected to the first trace and such that the rod is electrically connected to the second trace.

The method further includes the step of attaching to the board first and second conducting pins for electrically connecting the traces to a voltage sensing circuit. The pins are attached to the board such that the first and second pins are electrically connected to the first and second traces, respectively, and such that the pins are electrically insulated from each other. In the preferred embodiment, the board is a printed circuit board having a diameter larger than the outer diameter of the tube to facilitate attachment of the probe to a probe positioning device, such as a mechanical arm.

DESCRIPTION

Figure 1:
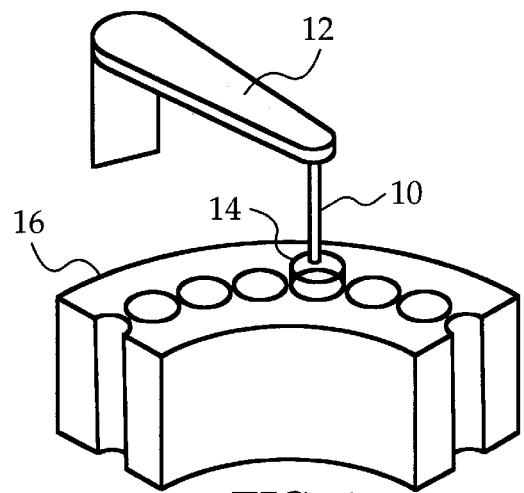
FIG. 1 is a schematic view of a mechanical arm equipped with a probe according to the invention.

A preferred embodiment of the invention is illustrated in FIGS. 1–9. FIG. 1 shows a probe 10 for dispensing and aspirating liquid into and out of a vessel 14. Vessel 14 is held in a rack 16 which is mounted on a carousel (not shown). Probe 10 is attached to a probe positioning device, such as a mechanical arm 12. Arm 12 is designed to position probe 10 in an appropriate vessel for aspirating or dispensing liquid. Such mechanical arms for positioning probes are well known in the art.

Figure 2:
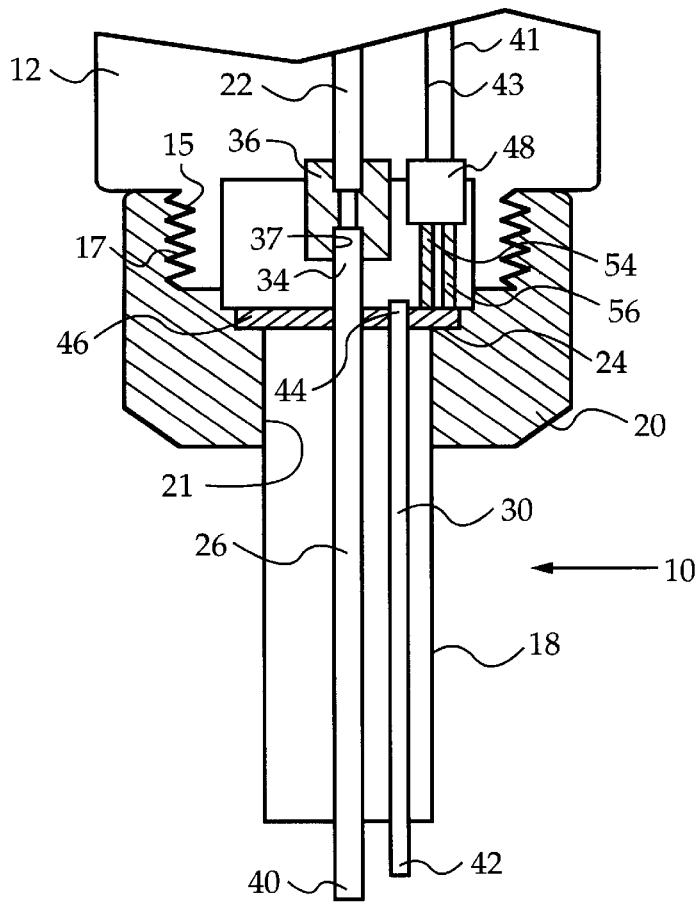
FIG. 2 is a cross sectional view of the probe and a portion of the mechanical arm of FIG. 1.

FIG. 2 shows a cross sectional view of probe 10 and a portion of arm 12. Probe 10 includes an electrically insulative tube 18, an electrically conductive fluid conduit 26, and an electrically conductive rod 30. Conduit 26 and rod 30 are made of a relatively inert material so that they do not chemically react with sample and reagent liquids. The inert material is preferably stainless steel or gold-coated copper.

Fluid conduit 26 has an inlet end 34 which protrudes from an upper end of tube 18. Fluid conduit 26 also has a discharge end 40 which protrudes from a lower end of tube 18. Discharge end 40 is immersed in the sample or reagent liquid during aspiration and dispensation. The middle section of conduit 26 between ends 34 and 40 is embedded in tube 18. Rod 30 has a sensing end 42, a contact end 44, and a middle portion between ends 42 and 44. Sensing end 42 protrudes from the lower end of tube 18 and contact end 44 protrudes from the upper end of tube 18. The middle portion of rod 30 is embedded in tube 18 such that rod 30 and conduit 26 are electrically insulated from each other.

Probe 10 also includes an insulative board 46 having a first hole for receiving inlet end 34 of conduit 26. Board 46 also has a second hole for receiving contact end 44 of rod 30. Ends 34 and 44 are inserted through the first and second holes respectively, and conduit 26 and rod 30 are attached to board 46 such that the bottom surface of board 46 contacts the upper end of tube 18. Probe 10 further includes first and second conducting pins 54 and 56. Pins 54 and 56 are attached to the top surface of board 46 such that the pins are electrically insulated from each other.

In the preferred embodiment, probe 10 is attached to arm 12 by a nut 20. Nut 20 has threads 17 for engaging threads 15 of arm 12. Board 46 has a diameter larger than the outer diameter of tube 18 to facilitate attachment of probe 10 to arm 12. Nut 20 has a bore 21 for receiving tube 18. Nut 20 also has a retaining rim 24 having an inner diameter slightly larger than the diameter of tube 18 and smaller than the diameter of board 46. To attach probe 10 to arm 12, tube 18 is inserted through bore 21 until board 46 contacts rim 24. Nut 20 is then screwed onto arm 12.

Arm 12 includes a zero-dead-volume fluid connector 36 connected to tubing 22. Tubing 22 is connected to a heater (not shown) for heating reagent and sample liquids. Fluid connector 36 has a reception channel 37 for receiving inlet end 34 of conduit 26. The diameter of inlet end 34 is selected such that inlet end 34 may be friction fit into channel 37. Arm 12 also includes an electrical connection box 48 for electrically contacting pins 54 and 56. Pins 54 and 56 are electrically connected to connection wires 43 and 41, respectively, through box 48. Wires 41 and 43 lead to first and second inputs, respectively, of a voltage sensing circuit, which will be explained in detail below.

Figure 3:
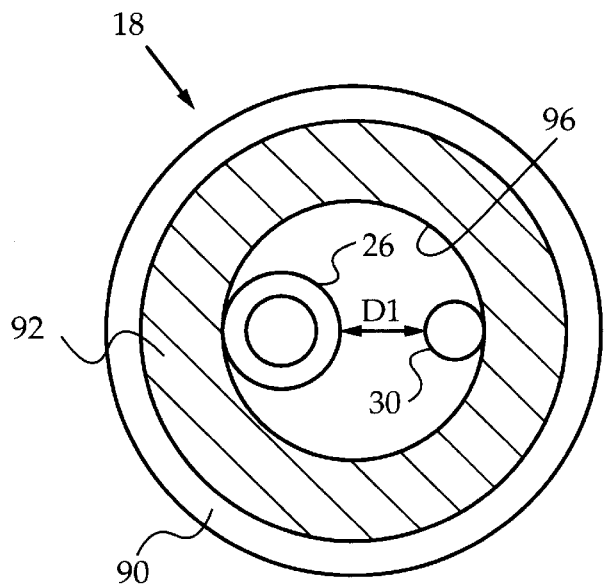
FIG. 3 is a cross sectional view of a fluid conduit and a rod positioned in a tube before a heating step according to the invention.

The production of probe 10 will now be explained. FIG. 3 shows a cross sectional view of tube 18 before a heating step of the invention is performed. Tube 18 has an inner layer 92 defining a central bore 96. Bore 96 extends the length of the tube. Tube 18 also has an outer layer 90 enclosing inner layer 92. Layers 90 and 92 are preferably made of chemically inert polymeric materials. Further, outer layer 90 is made of a heat-shrinkable material and inner layer 92 is made of a meltable material. Inner layer 92 has a lower melting point than outer layer 90.

In the preferred embodiment, outer layer 90 is made of tetrafluoroethylene (TEFLON™ TFE) and inner layer 92 is made of fluorinated ethylene propylene (TEFLON™ FEP). In an alternative embodiment, inner layer 92 is made of perfluoroalkoxy (TEFLON™ PFA). Suitable tubes having these specifications are commercially available from Zeus Industrial Products, Inc. located at 501 Boulevard Street, Orangeburg, S.C., 29115.

Conduit 26 and rod 30 are positioned in central bore 96 such that the inlet end of conduit 26 and the contact end of rod 30 protrude from the upper end of tube 18 and such that the discharge end of conduit 26 and the sensing end of rod 30 protrude from the lower end of tube 18. Conduit 26 and rod 30 are spaced apart a distance D1 in bore 96. Distance D1 is sufficiently large to ensure that conduit 26 and rod 30 are electrically insulated from each other after tube 18 is heated. In the preferred embodiment, distance D1 is at least 1.0 mm.

Figure 4:
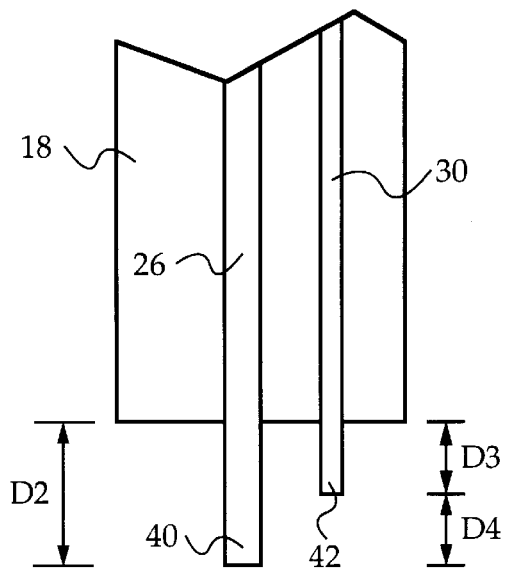
FIG. 4 is a schematic side view of portions of the tube, fluid conduit, and rod of FIG. 3.

FIG. 4 shows a more detailed view of the positioning of conduit 26 and rod 30 in tube 18. Conduit 26 is positioned such that discharge end 40 protrudes a first offset distance D2 from the lower end of tube 18. Rod 30 is positioned such that sensing end 42 protrudes a second offset distance D3 from the lower end of tube 18. The difference between offset distances D2 and D3 is a non-zero distance D4. Distance D4 is chosen to be larger than the average size of the bubbles present on the surface of the liquid to ensure that electrical contact between conduit 26 and rod 30 only occurs when discharge end 40 is immersed in liquid. An order of magnitude estimate for the size of air bubbles is 0.5 mm for a typical sample so that the difference between offset distances D2 and D3 is preferably in the range of 0.25 mm to 1.0 mm.

Following the positioning of conduit 26 and rod 30, tube 18 is heated such that outer layer 90 shrinks and inner layer 92 melts. In the preferred embodiment, tube 18 is heated in an oven at a temperature in the range of 170° to 210° C. for about 0.5 hours. Alternatively, tube 18 may be heated with a heat gun or any device capable of shrinking outer layer 90 and melting inner layer 92. As inner layer 92 melts, it flows into bore 96 to encapsulate the middle section of conduit 26 and the middle portion of rod 30.

Figure 5:
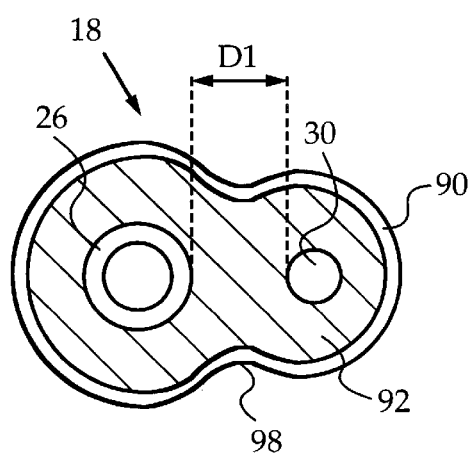
FIG. 5 is a cross sectional view of the fluid conduit, rod, and tube of FIG. 3 after the heating step according to the invention.

FIG. 5 shows a cross sectional view of the resulting structure. The middle section of conduit 26 and the middle portion of rod 30 are encapsulated in tube 18 such that conduit 26 is electrically insulated from rod 30 by melted inner layer 92. Further outer layer 90 is shrunk and inner layer 92 melted to form in tube 18 a longitudinal waist 98 between conduit 26 and rod 30. Waist 98 provides probe 18 with a cross sectional shape which reduces the likelihood of a liquid droplet forming on the lower end of probe 18 when the probe is not immersed in liquid. The surface tension associated with a droplet having a corresponding shape is very high, so that droplets will not adhere to probe 18. Thus, waist 98 effectively prevents liquid droplets from establishing electrical contact between conduit 26 and rod 18 when probe is not immersed in liquid.

Figure 6:
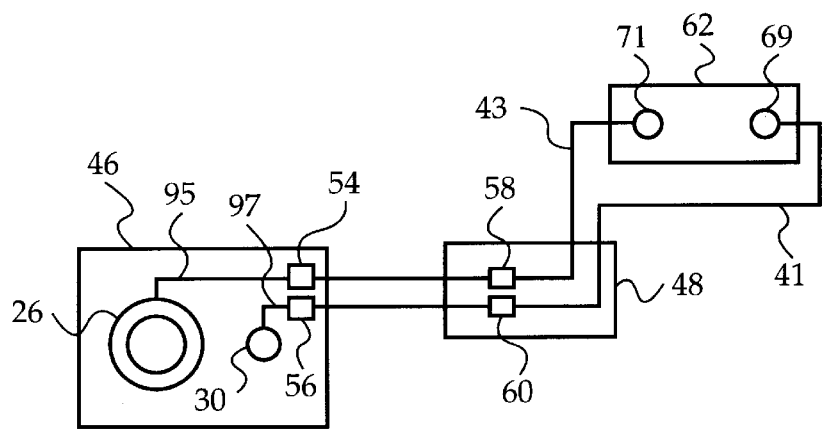
FIG. 6 is a schematic view of the electrical connections of the probe of FIG. 1.
Figure 7:
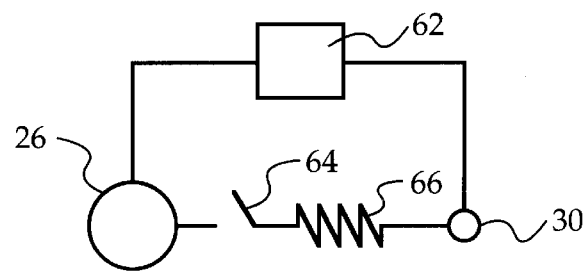
FIG. 7 is a simplified diagram illustrating a voltage sensing circuit according to the invention.

FIG. 6 shows a top schematic view of board 46, conduit 26, and rod 30. Following the heating of tube 18, the inlet end of conduit 26 is inserted through the first hole in board 46 and the contact end of rod 30 is inserted through the second hole in board 46. Board 46 has on its top surface a first electrically conductive trace 95 and a second electrically conductive trace 97. Traces 95 and 97 are located on board 46 such that they are electrically insulated from each other. Board 46 may be made of any material which is an electrical insulator and which is capable of supporting electrical traces. In the preferred embodiment, board 46 is a printed circuit board.

Conduit 26 and rod 30 are attached to the top surface of board 26 such that conduit 26 is electrically connected to first trace 95 and such that rod 30 is electrically connected to second trace 97. Conducting pins 54 and 56 are attached to the top surface of board 46 such that first pin 54 is electrically connected to first trace 95 and such that second pin 56 is electrically connected to second trace 97. Conducting pins 54 and 56 are also attached to the top surface of board 46 such that the pins are electrically insulated from each other.

In the preferred embodiment, conduit 26, rod 30, and pins 54 and 56 are soldered to the top surface of board 46. Also in the preferred embodiment, conduit 46 and rod 30 are attached to board 46 such that the bottom surface of board 46 contacts the upper end of tube 18, as shown in FIG. 2. Probe 10 is then attached to arm 12 with nut 20, as was previously described.

Referring again to FIG. 6, connection box 48 contains a first contact pad 58 and a second contact pad 60. When the probe is attached to arm 12, pin 54 electrically contacts first pad 58 and pin 56 electrically contacts second pad 60. Pad 60 is electrically connected by wire 41 to a first input 69 of a voltage sensing circuit 62. Pad 58 is electrically connected by wire 43 to a second input 71 of circuit 62.

In operation, probe 10 is used to transfer liquids between various vessels in a chemical analyzer. Referring again to FIG. 2, when discharge end 40 and sensing end 42 are located above a liquid surface, there is no electrical contact between fluid conduit 26 and rod 30. When probe 10 is immersed in liquid, however, the liquid electrically connects conduit 26 and rod 30. The two situations are depicted schematically in FIG. 7. When either conduit 26 or rod 30 is not in contact with the liquid, a schematic switch 64 is open. Immersing conduit 26 and rod 30 in the liquid effectively closes schematic switch 64. The liquid provides a resistance 66 between conduit 26 and rod 30. A voltage drop across resistance 66 is recorded by circuit 62.

Figure 8:
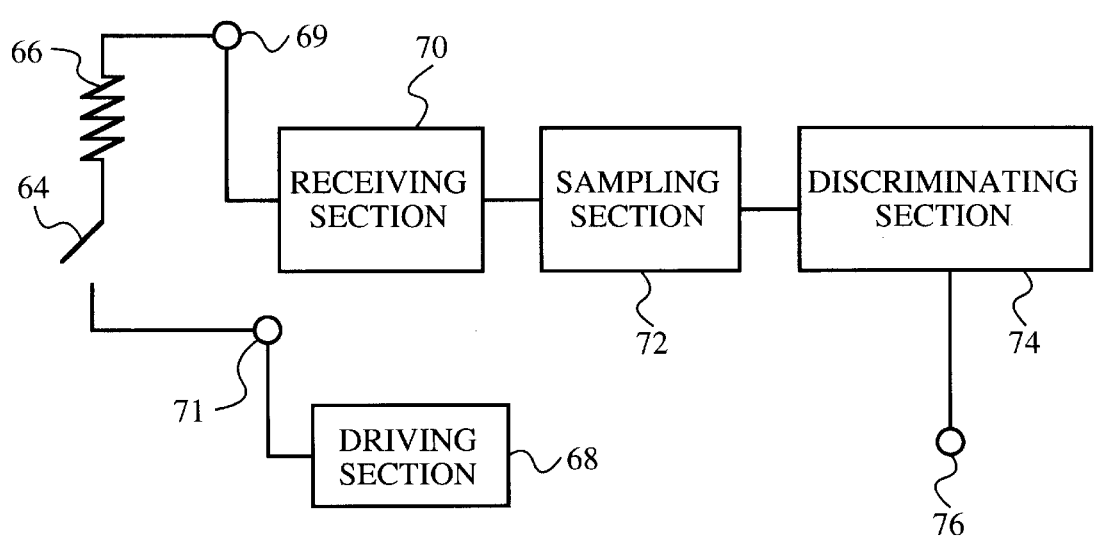
FIG. 8 is a schematic block diagram of the voltage sensing circuit of FIG. 7.

FIG. 8 is a simplified block diagram of voltage sensing circuit 62. Input 71 is connected to an oscillator driving section 68. Input 69 is connected to a probe receiver section 70. A sampling section 72 is also connected to receiver section 70. Sampling section 72 sends a periodic sampling signal to a discriminating section 74 when schematic switch 64 is closed. If discriminating section 74 receives a predetermined number of consecutive sampling signals, it sends a status signal to an output 76.

Figure 9:
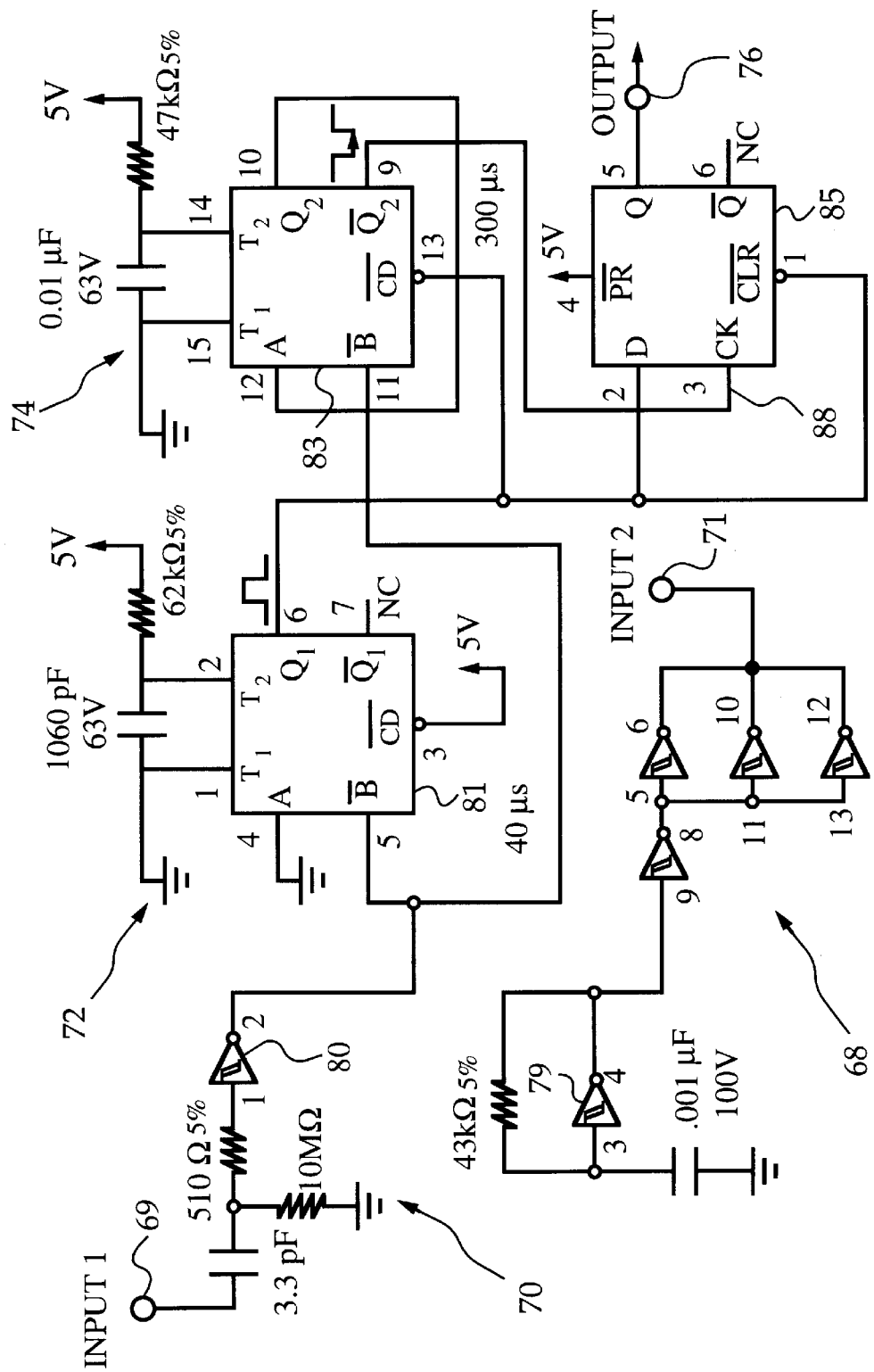
FIG. 9 is a detailed circuit diagram of the voltage sensing circuit of FIG. 7.

FIG. 9 shows a detailed circuit diagram of the voltage sensing circuit. Oscillator driving section 68 includes a simple RC oscillator built around a CMOS Schmitt trigger inverter 79. Inverter 79 is buffered at input 71 by additional Schmitt trigger inverters. Oscillator driving section 68 generates a square wave signal which is received by probe receiver section 70 when the schematic switch is closed. The square wave signal is capable of sourcing/sinking ±60 mA.

Probe receiver section 70 includes a CMOS Schmitt trigger inverter 80 and a high pass filter connected to a series resistor at the input of inverter 80. The series resistor at the input of inverter 80 is used to adjust the sensitivity of probe receiver section 70 to different fluid resistive properties. Since CMOS Schmitt trigger inverters require only 1 mA sink or source current to change output, probe receiver section 70 is sensitive to small changes in the current passing through fluid, i.e. through schematic resistor 66.

Sampling section 72 includes a precision monostable multivibrator 81 connected directly to the output of receiver section 70. Multivibrator 81 is configured as a retriggerable one-shot multivibrator with a period of 40 $\mu$s. Discriminating section 74 includes a second multivibrator 83 configured as a non-retriggerable one-shot multivibrator with a period of 300 $\mu$s. If both the fluid conduit and rod are immersed in liquid continuously for a period of 300 $\mu$s, multivibrator 81 sends 8 consecutive sampling signals and never resets multivibrator 83. Multivibrator 83 then sends a status signal to an input 88 of a chip 85. Chip 85 then sets output 76 to 5 V. Thus, the circuit determines that the fluid conduit has reached the liquid surface only if repeated samplings over a period of 300 $\mu$s show that both the fluid conduit and rod are immersed during that period.

SUMMARY, RAMIFICATIONS, AND SCOPE

Although the above description contains many specificities, these should not be construed as limitations on the scope of the invention, but merely as illustrations of the presently preferred embodiment. Many other embodiments of the invention are possible. For example, in alternative embodiments, the board attached to the fluid conduit and rod may be a section of substrate, a plastic board, or any other material having insulating properties.

Also in alternative embodiments, the probe may be attached to the mechanical arm by snap fitting, friction fitting, etc. In embodiments that include an attachment piece, such as a nut, for attaching the probe to the arm, the attachment piece may be separate from the probe or permanently affixed to the probe. Further, those skilled in the art will recognize that many different sensing circuits may be used with the probe. Additionally, the sensing circuits may be configured with different time periods for determining if the probe is immersed in liquid.

Therefore, the scope of the invention should be determined, not by examples given, but by the appended claims and their legal equivalents.

We claim:

1. A method of producing a probe for aspirating and dispensing liquid, the method comprising the steps of:
   a) providing an electrically insulative tube, an electrically conductive fluid conduit, and an electrically conductive rod, the tube having upper and lower ends, a heat-shrinkable outer layer, a meltable inner layer, and a central bore extending the length of the tube, the inner layer having a lower melting point than the outer layer, the conduit having an inlet end, a discharge end, and a middle section between the inlet and discharge ends, and the rod having a contact end, a sensing end, and a middle portion between the contact and sensing ends;
   b) positioning the conduit and the rod in the central bore such that the inlet end of the conduit and the contact end of the rod protrude from the upper end of the tube and such that the discharge end of the conduit and the sensing end of the rod protrude from the lower end of the tube; and
   c) heating the tube such that the outer layer shrinks and the inner layer melts to encapsulate the middle section of the conduit and the middle portion of the rod, wherein the outer layer shrinks and the inner layer melts to form in the tube a longitudinal waist between the conduit and the rod, and wherein the middle section of the conduit and the middle portion of the rod are encapsulated such that the conduit is electrically insulated from the rod.

2. The method of claim 16, further comprising the steps of:
   a) providing a board having a first hole for receiving the inlet end of the conduit, a second hole for receiving the contact end of the rod, and first and second electrically conductive traces, wherein the traces are electrically insulated from each other;
   b) inserting the inlet end of the conduit through the first hole and the contact end of the rod through the second hole;
   c) attaching the conduit and the rod to the board such that the conduit is electrically connected to the first trace and such that the rod is electrically connected to the second trace; and
   d) attaching to the board first and second conducting pins for electrically connecting the traces to a voltage sensing circuit, wherein the pins are attached to the board such that the first and second pins are electrically connected to the first and second traces, respectively, and such that the first and second pins are electrically insulated from each other.

3. The method of claim 2, wherein the board comprises a printed circuit board.

4. The method of claim 2, wherein the board has a top surface and a bottom surface, the traces are located on the top surface, the pins are attached to the top surface, and the conduit and the rod are attached to the board such that the bottom surface of the board contacts the upper end of the tube.

5. The method of claim 2, wherein the board has a diameter larger than the diameter of the tube to facilitate attachment of the probe to a probe positioning device.

6. The method of claim 2, wherein the conduit, the rod, and the pins are soldered to the board.

7. The method of claim 1, wherein the inner and outer layers comprise chemically inert polymeric materials.

8. The method of claim 1, wherein the outer layer comprises tetrafluoroethylene.

9. The method of claim 1, wherein the inner layer comprises a material selected from the group consisting of fluorinated ethylene propylene and perfluoroalkoxy.

10. The method of claim 1, wherein the tube is heated at a temperature in the range of 170° to 210° C. for about 0.5 hours.

11. The method of claim 1, wherein the conduit and the rod are positioned in the tube such that the discharge end of the conduit protrudes a first offset distance from the lower end of the tube and such that the sensing end of the rod protrudes a second offset distance from the lower end of the tube, and wherein the difference between the first and second offset distances is non-zero.

12. The method of claim 11, wherein the difference between the first and second offset distances is in the range of 0.25 mm to 1.0 mm.

* * * * *